US012639811B2

(12) United States Patent
Kanai et al.

(10) Patent No.: US 12,639,811 B2
(45) Date of Patent: May 26, 2026

(54) URINATION ANALYSIS METHOD, URINATION ANALYSIS DEVICE, AND NON-TRANSITORY COMPUTER READABLE RECORDING MEDIUM

(71) Applicant: PANASONIC HOLDINGS CORPORATION, Osaka (JP)

(72) Inventors: Hirofumi Kanai, Osaka (JP); Yuka Yamada, Nara (JP); Hideyuki Maehara, Osaka (JP)

(73) Assignee: Panasonic Housing Solutions Co., Ltd., Osaka (JP)

( * ) Notice: Subject to any disclaimer, the term of this patent is extended or adjusted under 35 U.S.C. 154(b) by 333 days.

(21) Appl. No.: 18/224,751

(22) Filed: Jul. 21, 2023

(65) Prior Publication Data

US 2023/0360206 A1 Nov. 9, 2023

Related U.S. Application Data

(63) Continuation of application No. PCT/JP2021/040784, filed on Nov. 5, 2021.

(Continued)

(30) Foreign Application Priority Data

Oct. 5, 2021 (JP) ................................. 2021-164145

(51) Int. Cl.
*G06K 9/00* (2022.01)
*A61B 5/20* (2006.01)
(Continued)

(52) U.S. Cl.
CPC ............ *G06T 7/0012* (2013.01); *A61B 5/208* (2013.01); *G01N 33/493* (2013.01); *G06T 7/20* (2013.01);
(Continued)

(58) Field of Classification Search
CPC .................................... G06K 9/00; G06T 7/90
(Continued)

(56) References Cited

U.S. PATENT DOCUMENTS 11,604,177 B1 * 3/2023 Park ........................... G06T 7/90
2005/0010128 A1 * 1/2005 Shiraishi ................ G01N 33/76
600/551

(Continued)

FOREIGN PATENT DOCUMENTS

JP 2020-516422 6/2020
JP 2020-124497 8/2020

OTHER PUBLICATIONS

Atsushi Isomura et al., "Flow Estimation Algorithm from Simulated Urination by Image Processing," IEEJ Transactions on Electronics, Information and Systems, vol. 136, No. 8, pp. 1194-1199, Aug. 2016.

(Continued)

*Primary Examiner* — Seyed H Azarian
(74) *Attorney, Agent, or Firm* — Greenblum & Bernstein, P.L.C.

(57) ABSTRACT

A urination analysis device that analyzes urination performs: acquiring image data captured by a camera which is located at a toilet to photograph a bowl of the toilet; calculating a urination pixel number being the number of pixels of an image showing urination from the image data when the urination by a user is detected by image recognition of the image data; calculating, on the basis of a change in the urination pixel number, a flow momentum value of the urination, a urine quantity, and a urine specific gravity; and outputting the flow momentum value, the urine quantity, and the urine specific gravity.

11 Claims, 7 Drawing Sheets

Related U.S. Application Data

(60) Provisional application No. 63/141,687, filed on Jan. 26, 2021.

(51) Int. Cl.

| | |
|---|---|
| *G01N 33/493* | (2006.01) |
| *G06T 7/00* | (2017.01) |
| *G06T 7/20* | (2017.01) |
| *G06T 7/90* | (2017.01) |
| *G16H 10/40* | (2018.01) |

(52) U.S. Cl.
    CPC .............. *G06T 7/90* (2017.01); *G16H 10/40* (2018.01); *G06T 2207/10024* (2013.01); *G06T 2207/30004* (2013.01); *G06T 2207/30196* (2013.01)

(58) Field of Classification Search
    USPC ........ 382/100, 103, 106–107, 128–134, 156, 382/162, 172–173, 181, 199, 214, 224, 382/254, 274, 286–291, 305, 312; 600/307, 309, 551
    See application file for complete search history.

(56) References Cited

U.S. PATENT DOCUMENTS

| | | | |
|---|---|---|---|
| 2018/0303466 A1 | 10/2018 | Kashyap et al. | |
| 2019/0298316 A1 | 10/2019 | Kashyap et al. | |
| 2022/0022791 A1* | 1/2022 | Korkor, II | A61B 5/7475 |
| 2022/0211354 A1* | 7/2022 | Kashyap | A61B 10/0038 |
| 2022/0237906 A1* | 7/2022 | Ueda | A47K 17/00 |
| 2022/0308040 A1* | 9/2022 | Tu | G01N 35/00871 |
| 2022/0333364 A1* | 10/2022 | Furuya | G01N 33/50 |

OTHER PUBLICATIONS

Atushi Isomura et al., "Effectiveness of Background Subtraction Method and Noise Reduction in Binary Images as for Estimating vol. of Liquid Imitating Male Urination," IEICE Technical Report, The Institute of Electronics, Information and Communication Engineers, vol. 114, No. 515, pp. 139-144, Mar. 2015.

International Search Report (ISR) from International Searching Authority (Japan Patent Office) in International Pat. Appl. No. PCT/JP2021/040784, dated Jan. 25, 2022, together with an English language translation.

* cited by examiner

FIG.5

| G/R (%) | | B/R (%) | | R | | G | | B | |
|---|---|---|---|---|---|---|---|---|---|
| Low | High | Low | High | Low | High | Low | High | Low | High |
| A1 | A2 | A3 | A4 | B1 | B2 | B1 | B2 | B1 | B2 |

URINATION ANALYSIS METHOD, URINATION ANALYSIS DEVICE, AND NON-TRANSITORY COMPUTER READABLE RECORDING MEDIUM

TECHNICAL FIELD

The present disclosure relates to a technology of analyzing urination from image data.

BACKGROUND ART

Patent Literature 1 discloses a technology of converting a color image into a grayscale image, calculating gradient magnitudes of an image from the grayscale image, binning the calculated gradient magnitudes of the image into a histogram of a fixed step size, inputting the histogram with the binned magnitudes to a classifier, such as a support vector machine, and determining stool or feces consistency.

However, the technology of Patent Literature 1 fails to consider flow momentum of urination, a urine quantity, and a urine specific gravity, and thus needs further improvement. Patent Literature 1: Japanese Unexamined Patent Publication No. 2020-516422

SUMMARY OF THE INVENTION

The present disclosure has been achieved to solve the drawbacks, and has an object of providing a technology of calculating at least one of flow momentum of urination, a urine quantity, and a urine specific gravity.

A urination analysis method according to one aspect of the present disclosure is a urination analysis method for a urination analysis device that analyzes urination. The urination analysis method includes: by a processor included in the urination analysis device, acquiring image data captured by a camera which is located at a toilet to photograph a bowl of the toilet; calculating a urination pixel number being the number of pixels of an image showing urination from the image data when the urination by a user is detected by image recognition of the image data; calculating, on the basis of a change in the urination pixel number, at least one of a flow momentum value indicating flow momentum of the urination, a urine quantity indicating a quantity of urine, and a urine specific gravity indicating a specific gravity of the urine; and outputting the at least one of the flow momentum value, the urine quantity, and the urine specific gravity.

This disclosure enables calculation of at least one of flow momentum of urination, a urine quantity, and a urine specific gravity.

BRIEF DESCRIPTION OF THE DRAWINGS

FIG. 5 is a table showing a urine condition.

DETAILED DESCRIPTION

Figure 1:
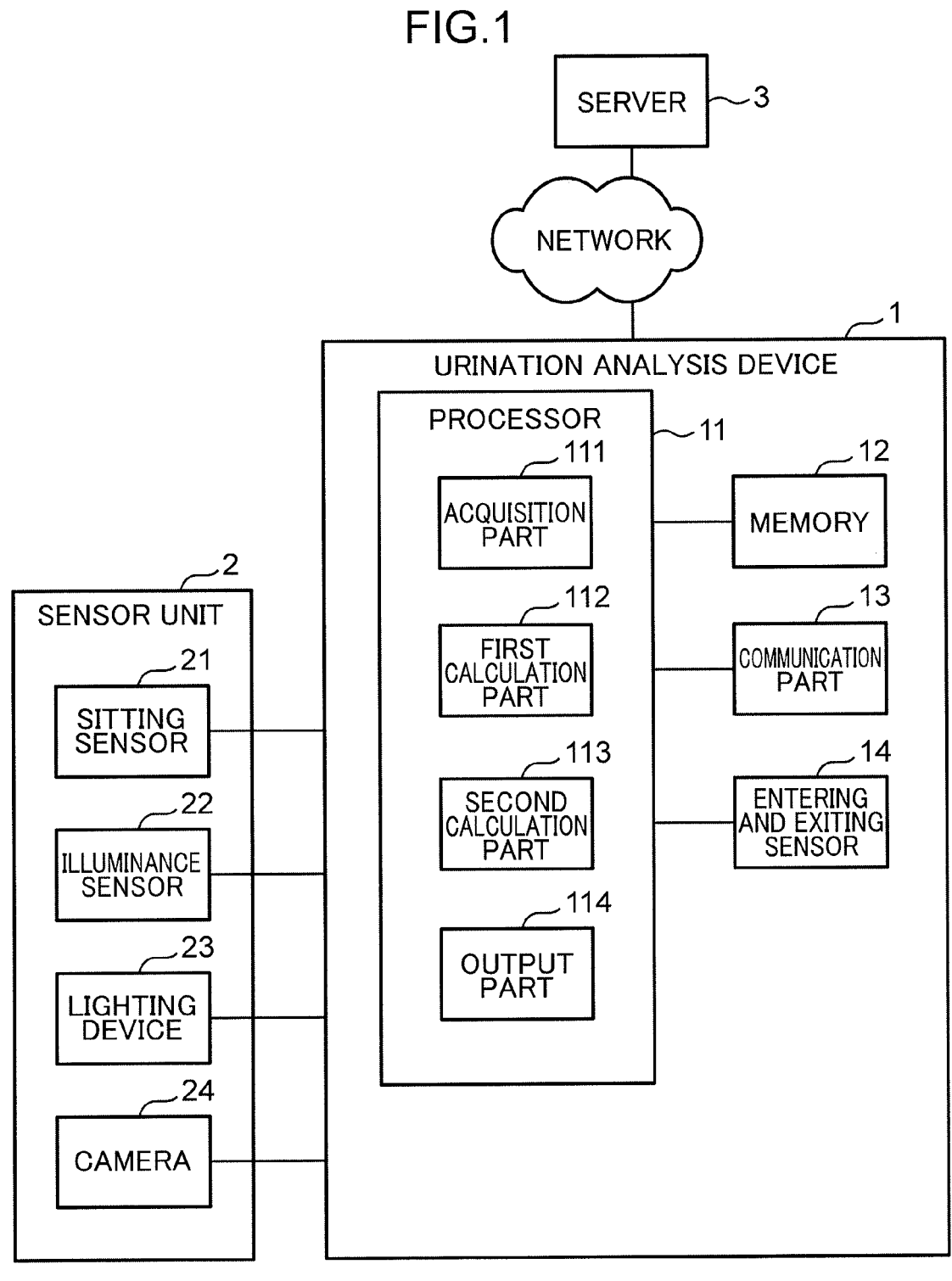
FIG. 1 is a diagram showing a configuration of a urination analysis system in an embodiment of the present disclosure.

Knowledge forming the basis of the present disclosure

In a care facility, excretion information including a frequency and a time of excretion about a care receiver is important to grasp a possible health risk of the care receiver. However, recordation of the excretion information by a caregiver or carer results in increasing the burden on the caregiver. Execution of the recordation of the excretion information by the caregiver near the care receiver increases a psychological burden on the care receiver. Thus, there has been a demand for recognition of excrement from image data captured by a camera which is located at a toilet, generation of excretion information based on a result of the recognition, and automatic recordation of the generated excretion information.

Such a person as an elderly person and a diabetic patient with a tendency of the lack of water intake has a larger urine specific gravity than others, and thus, the urine specific gravity serves as an important index for management of the health of the person. Flow momentum of urination decreases along with aging of a person, and thus, the flow momentum of urination also serves as an important index for management of the health of the person. Additionally, the elderly person with the tendency of the lack of water intake has a smaller urine quantity, and thus, the urine quantity also serves as an important index for management of the health of the person.

Under the circumstances, the present inventors having observed a change in a color of a pool part of a toilet after a urination start have found that the color of the pool part notably fades or becomes lighter concerning a person, such as an elderly person and a diabetic patient, having a large urine specific gravity in comparison with a person having a small urine specific gravity. The present inventors further having observed image data of the pool part from the urination start to a urination finish have found that flow momentum of urination and a urine quantity are calculatable from a change in the number of pixels of an image showing urination in the image data.

This disclosure has been achieved on the basis of the aforementioned findings or knowledge.

A urination analysis method according to one aspect of the present disclosure is a urination analysis method for a urination analysis device that analyzes urination. The urination analysis method includes: by a processor included in the urination analysis device, acquiring image data captured by a camera which is located at a toilet to photograph a bowl of the toilet; calculating a urination pixel number being the number of pixels of an image showing urination from the image data when the urination by a user is detected by image recognition of the image data; calculating, on the basis of a change in the urination pixel number, at least one of a flow momentum value indicating flow momentum of the urination, a urine quantity indicating a quantity of urine, and a urine specific gravity indicating a specific gravity of the urine; and outputting the at least one of the flow momentum value, the urine quantity, and the urine specific gravity.

According to this configuration, the urination pixel number being the number of pixels of an image showing urination in image data is calculated, at least one of a flow momentum value of the urination, a urine quantity, and a urine specific gravity is calculated on the basis of a change in the urination pixel number, and a calculation result is output. This configuration enables calculation of at least one of the flow momentum value, the urine quantity, and the urine specific gravity each serving as a useful index for management of health of a person.

In the urination analysis method, the flow momentum value may be calculated on the basis of a maximum value in increase amounts per unit time with respect to the urination pixel number.

According to this configuration, the flow momentum value is calculated on the basis of a maximum value in increase amounts per unit time with respect to the urination pixel number, and thus, accurate calculation of the flow momentum value is achieved.

In the urination analysis method, the urine quantity may be calculated on the basis of a first integral value being an integral value of increase amounts per unit time with respect to the urination pixel number.

According to this configuration, the urine quantity is calculated on the basis of the first integral value being an integral value of increase amounts per unit time with respect to the urination pixel number, and thus, accurate calculation of the urine quantity is achieved.

In the urination analysis method, the urine specific gravity may be calculated on the basis of a second integral value being an integral value of decrease amounts per unit time with respect to the urination pixel number.

According to this configuration, the urine specific gravity is calculated on the basis of the second integral value being an integral value of decrease amounts per unit time with respect to the urination pixel number, and thus, accurate calculation of the urine specific gravity is achieved.

In the urination analysis method, the flow momentum value may be calculated on the basis of the maximum value in the increase amounts and the urine specific gravity.

This configuration enables the flow momentum value to be increased in consideration of a quantity of urine sinking from a surface layer of the pool part into the bottom thereof during the urination, and achieves further accurate calculation of the flow momentum value.

In the urination analysis method, the urine quantity may be calculated on the basis of the first integral value and the urine specific gravity.

This configuration enables the urine quantity to be increased in consideration of the quantity of urine sinking from the surface layer of the pool part into the bottom thereof during the urination, and achieves further accurate calculation of the urine quantity.

In the urination analysis method, in the calculating of the flow momentum value, a maximum value in derivative values of the urination pixel number in a period from a urination start to a urination finish may be calculated as the maximum value in the increase amounts.

According to this configuration, the flow momentum value is calculated on the basis of a maximum value in derivative values of the urination pixel number per unit time in the period from the urination start to the urination finish, and thus, further accurate calculation of the flow momentum value is achieved.

In the urination analysis method, in the calculating of the urine quantity, an integral value of derivative values of the urination pixel number in a period from a urination start to a urination finish may be calculated as the first integral value.

According to this configuration, the urine quantity is calculated on the basis of the integral value of derivative values of the urination pixel number in the period from the urination start to the urination finish, and thus, further accurate calculation of the urine quantity is achieved.

In the urination analysis method, in the calculating of the urine specific gravity, an integral value of derivative values of the urination pixel number in a period from a urination finish to leaving of the user from the toilet may be calculated as the second integral value.

According to this configuration, the urine specific gravity is calculated on the basis of the integral value of derivative values of the urination pixel number in the period from the urination finish to the leaving from the toilet, and thus, further accurate calculation of the urine specific gravity is achieved.

In the urination analysis method, in the detecting of the urination, the urination may be detected when the image data includes pixel data in which a G/R value, a B/R value, an R value, a G value, and a B value satisfy a predetermined urine condition.

This configuration achieves accurate detection of the urination.

A urination analysis device according to another aspect of this disclosure is a urination analysis device that analyzes urination. The urination analysis device includes: an acquisition part that acquires image data captured by a camera which is located at a toilet to photograph a bowl of the toilet; a first calculation part that calculates a urination pixel number being the number of pixels of an image showing urination from the image data when the urination by a user is detected by image recognition of the image data; a second calculation part that calculates, on the basis of a change in the urination pixel number, at least one of a flow momentum value indicating flow momentum of the urination, a urine quantity indicating a quantity of urine, and a urine specific gravity indicating a specific gravity of the urine; and an output part that outputs at least one of the flow momentum value, the urine quantity, and the urine specific gravity.

With this configuration, it is possible to provide a urination analysis device that exerts operational effects equivalent to those of the urination analysis method described above.

A urination analysis program according to still another aspect of the disclosure is a urination analysis program causing a computer to serve as a urination analysis device that analyzes urination. The urination analysis program includes: causing the computer to execute: acquiring image data captured by a camera which is located at a toilet to photograph a bowl of the toilet; calculating a urination pixel number being the number of pixels of an image showing urination from the image data when the urination by a user is detected by image recognition of the image data; calculating, on the basis of a change in the urination pixel number, at least one of a flow momentum value indicating flow momentum of the urination, a urine quantity indicating a quantity of urine, and a urine specific gravity indicating a specific gravity of the urine; and outputting the at least one of the flow momentum value, the urine quantity, and the urine specific gravity.

With this configuration, it is possible to provide a urination analysis program that exerts operational effects equivalent to those of the urination analysis method described above.

This disclosure can be realized as a urination analysis system caused to operate by the urination analysis program. Additionally, it goes without saying that the computer program is distributable as a non-transitory computer readable storage medium like a CD-ROM, or distributable via a communication network like the Internet.

An embodiment which will be described below represents a specific example of the disclosure. Numeric values, shapes, constituent elements, steps, and the order of the steps described below are mere examples, and thus should not be construed to delimit the disclosure. Moreover, constituent elements which are not recited in the independent claims each showing the broadest concept among the constituent elements in the embodiments are described as selectable constituent elements. The respective contents are combinable with each other in the embodiment.

Embodiment

Figure 2:
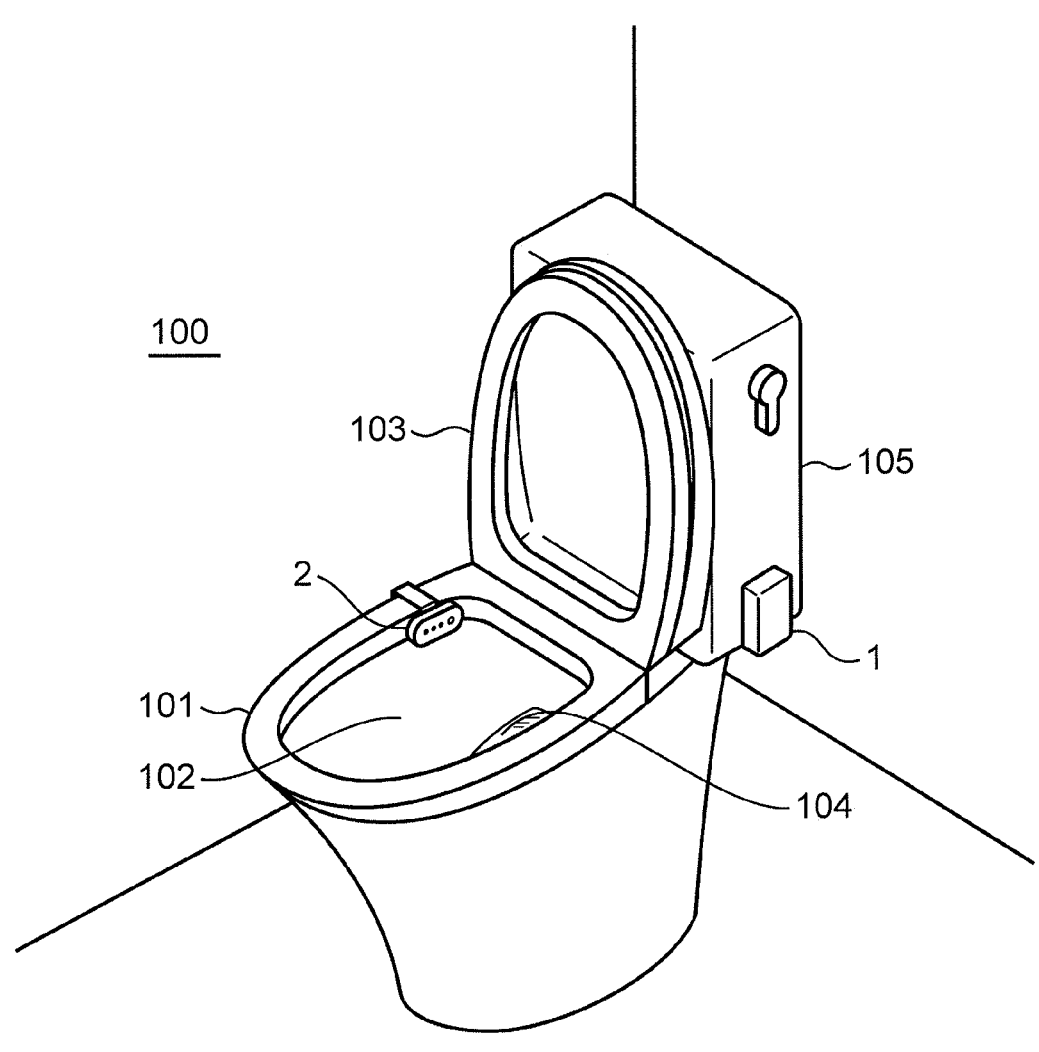
FIG. 2 is a view explaining arrangement positions of a sensor unit and a urination analysis device in the embodiment of the disclosure.

FIG. 1 is a diagram showing a configuration of a urination analysis system in an embodiment of the present disclosure. FIG. 2 is a view explaining arrangement positions of a sensor unit 2 and a urination analysis device 1 in the embodiment of the disclosure.

The urination analysis system shown in FIG. 1 includes the urination analysis device 1, the sensor unit 2, and a server 3. The urination analysis device 1 analyzes urination by a user on the basis of image data captured by a camera 24. The urination analysis device 1 is arranged, for example, on a side surface of a water reservoir tank 105 as shown in FIG. 2. However, this is just an example, and the urination analysis device 1 may be arranged on a wall of a toilet room or imbedded in the sensor unit 2. Thus, an arrangement position of the device is not particularly limited. The urination analysis device 1 is connected to the server 3 via a network. The network includes, for example, a wide area network like the internet. The server 3 manages excretion information about the user generated by the urination analysis device 1.

The sensor unit 2 is attached, for example, onto a fringe part 101 of a toilet 100 as shown in FIG. 2. The sensor unit 2 is communicably connected to the urination analysis device 1 via a predetermined communication channel. The communication channel may include a wireless channel, such as the Bluetooth (registered mark) or a wireless LAN, or a wired LAN.

As shown in FIG. 2, the toilet 100 includes the fringe part 101 and a bowl 102. The fringe part 101 is located at an upper end of the toilet 100 and defines an opening section of the toilet 100. The bowl 102 is located below the fringe part 101 to receive feces and urine.

The bowl 102 has a bottom provided with a pool part 104 for pooling water (pooled water). The pool part 104 is provided with an unillustrated drain hole. The feces and the urine excreted in the bowl 102 is caused to flow to a sewage pipe through the drain hole. In other words, the toilet 100 is in the form of a toilet of a flush type. A toilet seat 103 is provided on the top of the toilet 100 to allow the user to sit thereon. The toilet seat 103 is rotatable upward and downward. The user sits on the toilet seat 103 lowered to lie on the fringe part 101. The water reservoir tank 105 that stores flush water to cause the feces and the urine to flow is provided in the rear of the toilet 100.

Referring back to FIG. 1, the sensor unit 2 includes a sitting sensor 21, an illuminance sensor 22, a lighting device 23, and the camera 24. Each of the sitting sensor 21 and the illuminance sensor 22 serves as an example of a sensor that detects sitting and leaving of the user onto and from the toilet 100.

The sitting sensor 21 is arranged at the toilet 100 to measure a distance to the buttocks of the user sitting on the toilet 100. The sitting sensor 21 is configured by, for example, a distance measurement sensor to measure a distance value indicating the distance to the buttocks of the user sitting on the toilet 100. One example of the distance measurement sensor is an infrared distance measurement sensor. The sitting sensor 21 measures the distance value at a predetermined sampling rate, and inputs the measured distance value to the urination analysis device 1 at a predetermined sampling rate. The sitting sensor 21 serves as an example of the sensor that detects a sitting state of the user. The distance value serves as an example of sensing data indicating each of sitting and leaving of the user.

The illuminance sensor 22 is arranged at the toilet 100 to measure illuminance in the bowl 102. The illuminance sensor 22 measures illuminance or an illuminance value in the bowl 102 at a predetermined sampling rate, and inputs the measured illuminance value to the urination analysis device 1 at a predetermined sampling rate. The illuminance value serves as an example of the sensing data indicating each of the sitting and the leaving of the user.

The lighting device 23 is arranged at the toilet 100 to light up the inside of the bowl 102. The lighting device 23 is, for example, a white LED. For instance, the lighting device 23 is turned on under a control by a processor 11 when the processor 11 detects sitting of the user on the basis of sensing data from the sitting sensor 21 or the illuminance sensor 22, and is turned off under a control by the processor 11 when the processor 11 detects leaving of the user on the basis of sensing data from the sitting sensor 21 or the illuminance sensor 22. The lighting by the lighting device 23 ensures necessary illuminance for the camera 24 to photograph the bowl 102.

The camera 24 is located at the toilet 100 to photograph the bowl 102. For instance, the camera 24 has a high sensitivity and a wide angle, and is configured to capture a color image having an R (red) component, a G (green) component, and a B (blue) component. The camera 24 photographs an inner part of the bowl 102 at a predetermined frame rate, and transmits obtained image data to the urination analysis device 1 at a predetermined sampling rate.

The urination analysis device 1 includes the processor 11, a memory 12, a communication part 13, and an entering and exiting sensor 14.

For instance, the processor 11 includes a center processing unit (CPU) or an ASIC (application specific integrated circuit). The processor 11 has an acquisition part 111, a first calculation part 112, a second calculation part 113, and an output part 114. Each of the acquisition part 111 to the output part 114 may be realized when the CPU executes a urination analysis program, or may be established in the form of a dedicated hardware circuit.

The acquisition part 111 acquires the image data captured by the camera 24 at a predetermined sampling rate. The acquisition part 111 acquires the distance value measured by the sitting sensor 21 at a predetermined sampling rate. The acquisition part 111 further acquires the illuminance value measured by the illuminance sensor 22 at a predetermined sampling rate.

The first calculation part 112 calculates a urination pixel number being the number of pixels of an image showing urination from image data when the urination by a user is detected by image recognition of the image data acquired by the acquisition part 111.

The image recognition will be described in detail below. Specifically, the first calculation part 112 calculates a G/R value and a B/R value on the basis of an R value, a G value, and a B value each included in the image data acquired by the acquisition part 111. The first calculation part 112 may then detect the urination by the user when the image data includes pixel data in which a G/R value, a B/R value, an R value, a G value, and a B value satisfy a predetermined urine condition. The urine condition will be described later.

The G/R value means a value obtained by dividing the G value by the R value and expressed with "%". The B/R value means a value obtained by dividing the B value by the R value and expressed with "%". The R value represents a gradation value of an R (red) component of pixel data, the G value represents a gradation value of a G (green) component of the pixel data, and the B value represents a gradation value of a B (blue) component of the pixel data. Each of the R value, the G value, and the B value takes, for example, a value of eight bits (0 to 255). However, this is just an example, and each of the R value, the G value, and the B value may be expressed with another bit number.

The first calculation part 112 may count the number of pixels of pixel data that satisfies the urine condition, and calculates the counted number of pixels as the urination pixel number. The urination pixel number is the number of pixels of an image showing urination.

The first calculation part 112 may set a detection area D1 (FIG. 3) on the image data acquired by the acquisition part 111, and determine the urination by the user when the detection area D1 includes pixel data that satisfies the urine condition. The first calculation part 112 may further count the number of pixels of pixel data that satisfies the urine condition in the detection area D1, and calculates the counted number of pixels as the urination pixel number.

Figure 3:
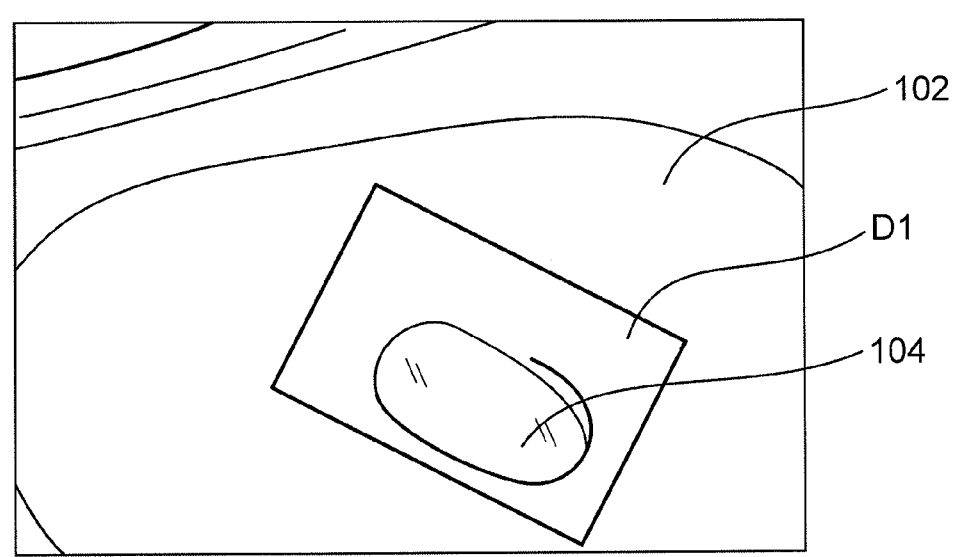
FIG. 3 shows a detection area.

FIG. 3 shows the detection area D1. The detection area D1 denotes a rectangular area containing the pool part 104 of the toilet. The first calculation part 112 may read out setting information from the memory 12, and set the detection area D1 on the image data in accordance with the setting information. The setting information indicates predetermined coordinate information indicating a coordinate for the detection area D1 in the image data. The toilet 100 is designed to receive excrement in the pool part 104. Thus, setting of the detection area D1 to the pool part 104 and detection of the excrement from the detection area D1 lead to a smaller processing burden than a burden in detection of excrement from whole image data.

The second calculation part 113 calculates, on the basis of a change in the urination pixel number, at least one of a flow momentum value indicating flow momentum of the urination, a urine quantity indicating a quantity of urine, and a urine specific gravity indicating a specific gravity of the urine. Hereinafter, the second calculation part 113 is described to calculate all the flow momentum value, the urine quantity, and the urine specific gravity.

The second calculation part 113 may calculate the flow momentum value on the basis of a maximum value in increase amounts per unit time with respect to the urination pixel number calculated by the first calculation part 112. Here, the second calculation part 113 may calculate, as the maximum value in the increase amounts, a maximum value in derivative values of the urination pixel number in a urination period from a urination start to a urination finish.

The second calculation part 113 may calculate the urine quantity on the basis of a first integral value being an integral value of increase amounts per unit time with respect to the urination pixel number. Here, the second calculation part 113 may calculate, as the first integral value, an integral value of derivative values of the urination pixel number in the urination period.

The second calculation part 113 may calculate the urine specific gravity on the basis of a second integral value being an integral value of decrease amounts per unit time with respect to the urination pixel number. Here, the second calculation part 113 may calculate, as the second integral value, an integral value of derivative values of the urination pixel number in a period from a urination finish to leaving of the user from the toilet 100.

The output part 114 generates excretion information including the flow momentum value, the urine quantity, and the urine specific gravity calculated by the second calculation part 113, and outputs the generated excretion information. The output part 114 may transmit the excretion information to the server 3 by using the communication part 13, or may cause the memory 12 to store the excretion information. The excretion information may include a urination time, image data including an image showing urination, and sensing data from the sitting sensor 21 and the illuminance sensor 22.

For instance, the memory 12 includes a storage device, such as a RAM (Random Access Memory), an SSD (Solid State Drive) or a flash memory, for storing various kinds of information. The memory 12 stores, for example, the excretion information, reference toilet color data, and the setting information. The memory 12 may be a portable memory like a USB (Universal Serial Bus) memory.

The communication part 13 includes a communication circuit serving to connect the urination analysis device 1 to the server 3 via the network. The communication part 13 serves to connect the urination analysis device 1 and the sensor unit to each other via the communication channel. The excretion information associates, for example, information about an occurrence of excretion (defecation, urination, and bleeding) with daily time information indicating an excretion date and time. For instance, the urination analysis device 1 may generate excretion information per day and transmit the generated excretion information to the server 3.

The entering and exiting sensor 14 includes, for example, a distance measurement sensor. The entering and exiting sensor 14 detects entering of the user into a toilet room where the toilet 100 is provided. Here, the distance measurement sensor constituting the entering and exiting sensor 14 has a lower measurement accuracy but a wider detection range than the distance measurement sensor constituting the sitting sensor 21. Examples of the distance measurement sensor include an infrared distance measurement sensor. The entering and exiting sensor 14 may include, for example, a human sensor in place of the distance measurement sensor. The human sensor detects the user located within a predetermined distance to the toilet 100.

Figure 4:
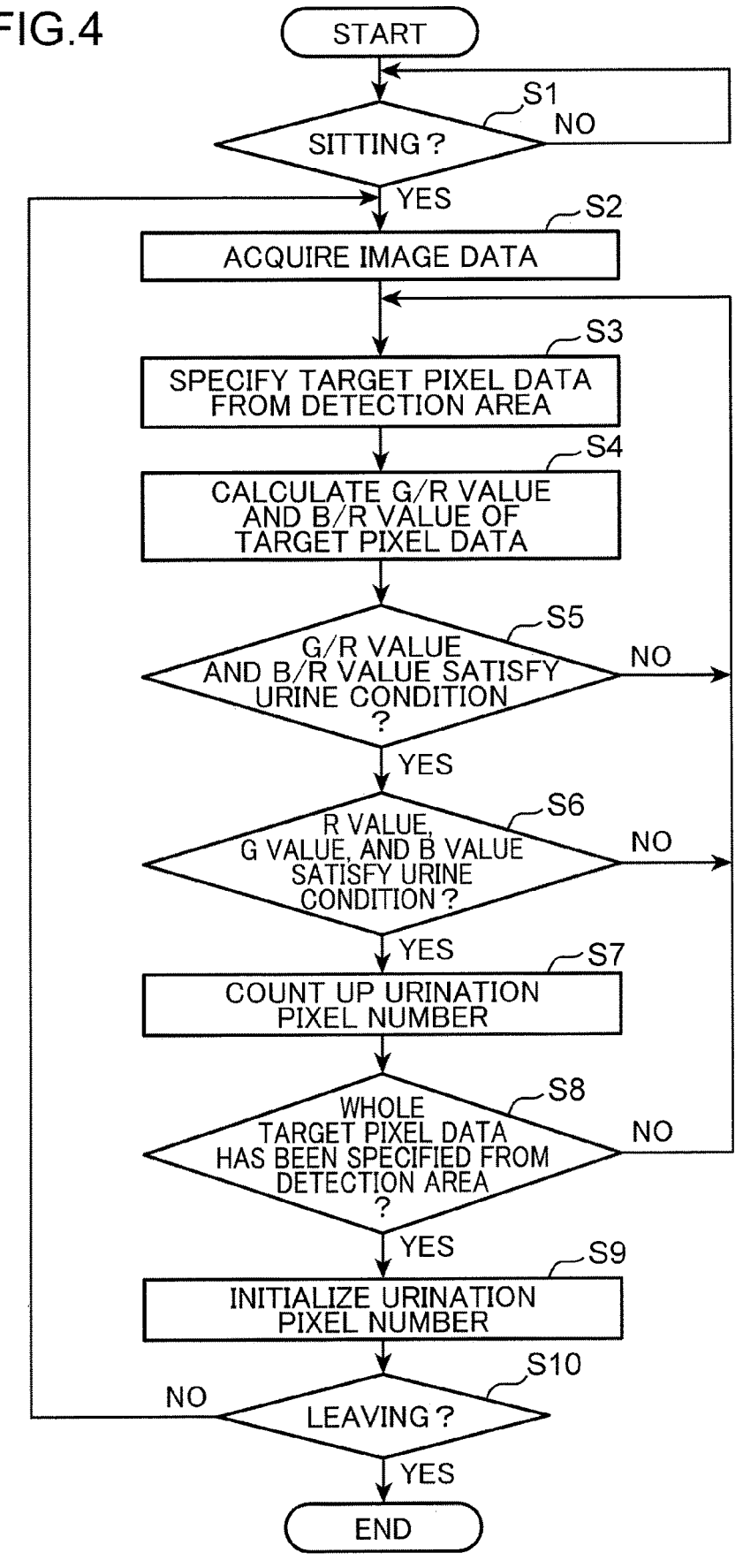
FIG. 4 is a flowchart showing an example of a process by the urination analysis device in the embodiment of the disclosure.

Heretofore, the configuration of the urination analysis system is described. Next, a process by the urination analysis device 1 will be described. FIG. 4 is a flowchart showing an example of the process by the urination analysis device 1 in the embodiment of the disclosure.

In step S1, the first calculation part 112 determines whether a user sits on the toilet 100. Here, the first calculation part 112 determines that the user sits when a distance value acquired from the sitting sensor 21 by the acquisition part 111 reaches a sitting detection threshold or smaller (YES in step S1), and leads the process to step S2. When the distance value is larger than the sitting detection threshold (NO in step S1), the first calculation part 112 makes the process wait in step S1 in standby. The sitting detection threshold can take an appropriate value, e.g., 10 cm, 15 cm, or 20 cm.

In step S2, the acquisition part 111 acquires image data from the camera 24.

In step S3, the first calculation part 112 sets the detection area D1 on the image data acquired by the acquisition part 111, and specifies target pixel data from the detection area D1. Here, the target pixel data is specified, for example, in the raster scanning order.

In step S4, the first calculation part 112 calculates a G/R value and a B/R value from an R value, a G value, and a B value of the target pixel data.

In step S5, the first calculation part 112 determines whether each of the G/R value and the B/R value satisfies a urine condition. The process proceeds to step S6 when each of the G/R value and the B/R value satisfies the urine condition (YES in step S5), and the process returns to step S3 to specify subsequent target pixel data when each of the G/R value and the B/R value dissatisfies the urine condition (NO in step S5).

In step S6, the first calculation part 112 determines whether each of the R value, the G value, and the B value satisfies the urine condition. The process proceeds to step S7 when each of the R value, the G value, and the B value satisfies the urine condition (YES in step S6), and the process returns to step S3 to specify subsequent target pixel data when each of the R value, G value, and the B value dissatisfies the urine condition (NO in step S6).

FIG. 5 is a table showing the urine condition. In FIG. 5, the sign "Low" indicates a lower limit threshold of a urine condition satisfying range, and the sign "High" indicates an upper limit threshold of the urine condition satisfying range.

The urine condition includes a condition that the G/R value is A1% or more to A2% or less and the B/R value is A3% or more to A4% or less, and further the R value is B1 or more to B2 or less, the G value is B1 or more to B2 or less, and the B value is B1 or more to B2 or less. However, A3% is less than A1%, and A4% is less than A2%. Further, B2 may indicate a maximum value in gradation values.

In detail, for instance, A1 indicates 80 or more to 90 or less, and preferably 83 or more to 87 or less.

For instance, A2 indicates 100 or more to 110 or less, and preferably 103 or more to 107 or less.

For instance, A3 indicates 45 or more to 55 or less, and preferably 48 or more to 52 or less.

A4 indicates 92 or more to 103 or less, and preferably 95 or more to 99 or less.

For instance, when the image data takes eight bits, B1 indicates 95 or more to 105 or less, and preferably 98 or more to 102 or less. When the image data takes a predetermined number of bits, B1 indicates, for example, 37% or more to 41% or less, and preferably 38% or more to 40% or less.

For instance, when the image data takes eight bits, B2 indicates 245 or more to 255 or less, and preferably 250 or more to 255 or less. When the image data takes a predetermined number of bits, B2 indicates, for example, 96% or more to 100% or less, and preferably 98% or to 100% or less.

Here, the urine condition may exclude the condition about each of the R value, the G value, and the B value.

In step S7, the first calculation part 112 counts up the urination pixel number.

In step S8, the first calculation part 112 determines whether whole target pixel data has been specified from the detection area D1. The process proceeds to step S9 when the whole pixel data has been specified (YES in step S8), and the process returns to step S3 to specify subsequent target pixel data when pixel data remains to be specified (NO in step S8).

In step S9, the first calculation part 112 sets the urination pixel number to "0" to initialize the urination pixel number. This is preparation for counting the urination pixel number about the subsequent target pixel data.

In step S10, the first calculation part 112 determines whether the user leaves the toilet 100.

Here, the first calculation part 112 may determine that the user leaves the toilet 100 when a distance value acquired from the sitting sensor 21 by the acquisition part 111 continuously exceeds a sitting detection threshold for a predetermined period or longer. The process finishes when the user leaves (YES in step S10), and the process returns to step S2 to acquire subsequent pixel data when the user does not leave (NO in step S10).

Figure 6:
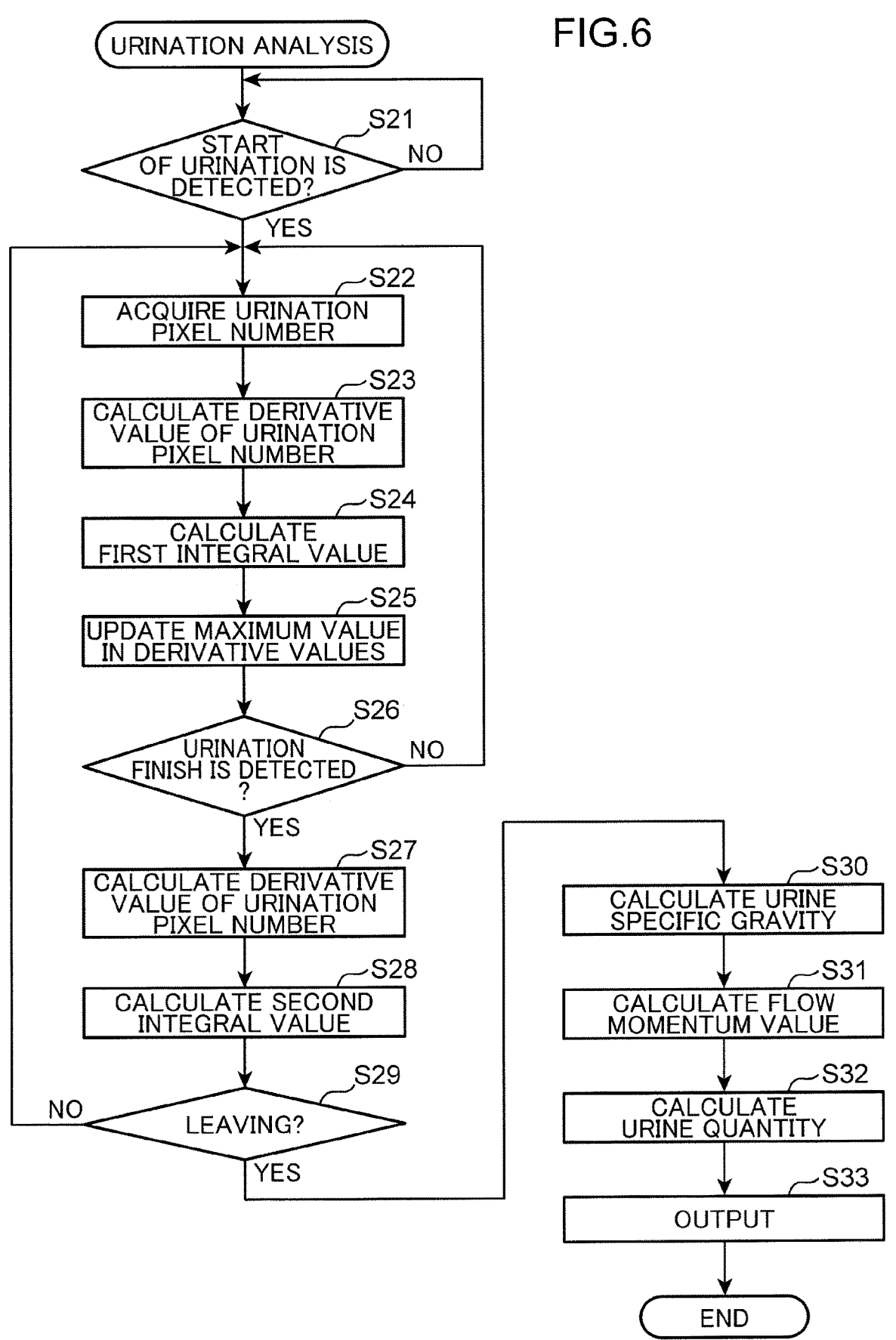
FIG. 6 is a flowchart showing an example of a urination analysis.

FIG. 6 is a flowchart showing an example of a urination analysis. The urination analysis includes calculating a flow momentum value, a urine quantity, and a urine specific gravity from image data. The flowchart in FIG. 6 parallels the flowchart in FIG. 4.

In step S21, the first calculation part 112 detects a urination start. The first calculation part 112 here may determine that the user has started urination in a case where pixel data that satisfies the urine condition is initially detected after detection of the sitting of the user (YES in step 1) in the flowchart in FIG. 4. The pixel data that satisfies the urine condition represents pixel data whose G/R value, B/R value, R value, G value, and B value satisfy the urine condition shown in FIG. 5 as described above. The first calculation part 112 may determine that the user has started the urination when a predetermined number of or more pixels of pixel data that satisfies the urine condition are detected.

In step S22, the second calculation part 113 acquires the urination pixel number. The second calculation part 113 may acquire the latest urination pixel number calculated in step S7 in FIG. 4. In this manner, the latest pixel number is acquired in step S22 per repetition of the flowchart in FIG. 6 to obtain time-series data of the urination pixel number.

In step S23, the second calculation part 113 calculates a derivative value $\Delta P$ of the urination pixel number. One example of the derivative value $\Delta P$ represents a value of change amounts per unit time with respect to the urination pixel number. One example of the unit time is a sampling cycle. It is seen from these perspectives that the second calculation part 113 may calculate the derivative value $\Delta P(t)$ by subtracting the urination pixel number $P(t-1)$ at a one-previous sample point from the urination pixel number $P(t)$ at a newest sampling point (t). The unit time may be n-times ("n" is an integer) of the sampling cycle. The derivative value $\Delta P(t)$ may be a value obtained by dividing change amounts per unit time with respect to the urination pixel number by the time unit.

In step S24, the second calculation part 113 calculates a first integral value $TP1(t)$ by adding the derivative value $\Delta P(t)$ calculated in step S23 to a first integral value $TP1(t-1)$ recorded in the memory 12. The first integral value $TP1(t)$ is an integral value of derivative values $\Delta P$ from a urination start to a current point. In a period from the urination start to a certain time point immediately before the urination finish, the urination pixel number increases, and thus, each derivative value $\Delta P(t)$ takes a positive value. By contrast, the urination pixel number starts to decrease in a transition to the urination finish, and thus, each derivative value $\Delta P(t)$ takes a negative value. The second calculation part 113 may calculate the first integral value $TP1(t)$ by adding only positive derivative values $\Delta P(t)$.

In step S25, when a latest derivative value $\Delta P(t)$ is larger than a maximum value $\Delta P_{max}$ in derivative values $\Delta P$ recorded in the memory 12, the second calculation part 113 updates the maximum value $\Delta P_{max}$ to the latest derivative value $\Delta P(t)$. By contrast, when the latest derivative value $\Delta P(t)$ is equal to or smaller than the maximum value $\Delta P_{max}$, the second calculation part 113 avoids updating the maximum value $\Delta P_{max}$. The maximum value $\Delta P_{max}$ consequently indicates a maximum value in the derivative values $\Delta P$ from the urination start to the current point.

In step S26, the second calculation part 113 detects the urination finish. The second calculation part 113 may detect the urination finish when the urination pixel number continuously decreases for a predetermined period. In detail, the second calculation part 113 may detect the urination finish when a negative derivative value $\Delta P$ continues for the predetermined period. The predetermined period can take an appropriate value, e.g., 0.1 seconds, 0.5 second, 1 second, and 2 seconds.

The process proceeds to step S27 when the urination finish is detected (YES in step S26), and the process returns to step S22 when the urination finish is not detected (NO in step S26).

In step S27, the second calculation part 113 calculates a derivative value $\Delta P(t)$.

In step S28, the second calculation part 113 calculates a second integral value $TP2(t)$ by adding the derivative value $\Delta P(t)$ calculated in step S27 to a second integral value $TP2(t-1)$ recorded in the memory 12. The second integral value $TP2(t)$ is an integral value of derivative values $\Delta P$ from the urination finish to a current point. After the urination finish, each derivative value $\Delta P$ basically takes a negative value since the urination pixel number basically does not increase. Accordingly, the second integral value $TP2(t)$ also takes a negative value. The second calculation part 113 may calculate the second integral value $TP2(t)$ by adding only negative derivative values $\Delta P(t)$.

In step S29, the first calculation part 112 determines whether the user leaves the toilet 100. Details of the step are the same as those of step S10 in FIG. 4. The process proceeds to step S30 when the leaving of the user is determined (YES in step S29), and the process returns to step S22 when no leaving of the user is determined (NO in step S29).

In step S30, the second calculation part 113 calculates, as a urine specific gravity, an absolute value of the second integral value TP2 calculated in step S28. The reason why the absolute value of the second integral value TP2 is calculated as the urine specific gravity is to allow the second integral value TP2 to take a positive value. However, this is just an example, and the second calculation part 113 may directly calculate the second integral value TP2 as the urine specific gravity.

In step S31, the second calculation part 113 calculates a flow momentum value on the basis of the maximum value $\Delta P_{max}$ updated in step S25 and the urine specific gravity calculated in step S30. In detail, under the definitions of the urine specific gravity as "a", the flow momentum as "β", and a predetermined constant as "C1", the second calculation part 113 calculates the flow momentum value β by using the following equation (1).

$$\beta = \Delta P_{max} \times a \times C1 \tag{1}$$

A quantity of urine sinking into the bottom of the pool part 104 increases as the urine specific gravity a is greater, and a maximum value $\Delta P_{max}$ decreases due to the sinking urine quantity. Accordingly, the flow momentum value is estimated to be small. The second calculation part 113 here calculates a flow momentum value by using the equation (1) to increase the flow momentum value estimated to be small. The constant C1 is predetermined to convert $\Delta P_{max} \times a$ into the flow momentum value.

In step S32, the second calculation part 113 calculates a urine quantity on the basis of the first integral value TP1 calculated in step S24 and the urine specific gravity a. In detail, under the definitions of the urine quantity as "γ" and the predetermined constant as "C2", the second calculation part 113 calculates the urine quantity γ by using the following equation (2).

$$\gamma = TP1 \times a \times C2 \tag{2}$$

The quantity of the urine sinking into the bottom of the pool part 104 increases as the urine specific gravity a is greater, and a first integral value TP1 decreases due to the sinking urine quantity. Accordingly, the urine quantity is estimated to be small. The second calculation part 113 here calculates a urine quantity by using the equation (2) to increase the urine quantity estimated to be small. The constant C2 is predetermined to convert $TP1 \times a$ into the urine quantity.

In step S33, the output part 114 generates excretion information including the urine specific gravity, the flow momentum value, and the urine quantity, and transmits the excretion information to the server 3 by using the communication part 13.

Figure 7:
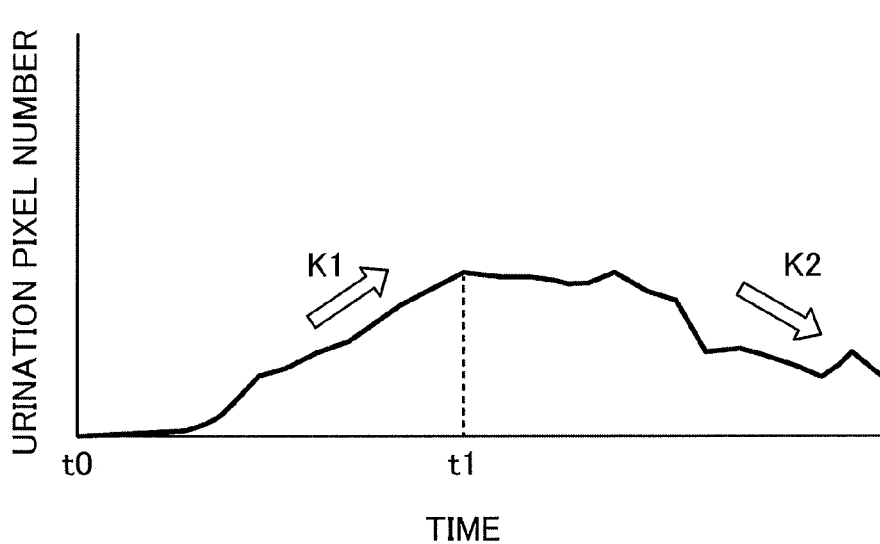
FIG. 7 is a graph showing a change in the urination pixel number over time about a person having a small flow momentum value and a large urine specific gravity.

FIG. 7 is a graph showing a change in the urination pixel number over time about a person having a small flow momentum value and a large urine specific gravity. In FIG. 7, the vertical axis shows the urination pixel number and the horizontal axis shows a time. This is applicable to the graph in FIG. 8.

A urination start is detected at a time t0. A urination finish is detected at a time t1. In a urination period from the time t0 to the time t1, a urine quantity in the pool part 104 increases, and accordingly, the urination pixel number increases with an average slope K1. After the time t1, urine in the surface layer of the pool part 104 gradually sinks into the bottom of the pool part 104 due to the urine specific gravity, and hence, the urination pixel number gradually decreases with an average slope K2. Thus, the second integral value TP2 increases as the quantity of the urine sinking into the bottom of the pool part 104 increases. The urine specific gravity also increases as the quantity of the urine sinking into the bottom increases.

Figure 8:
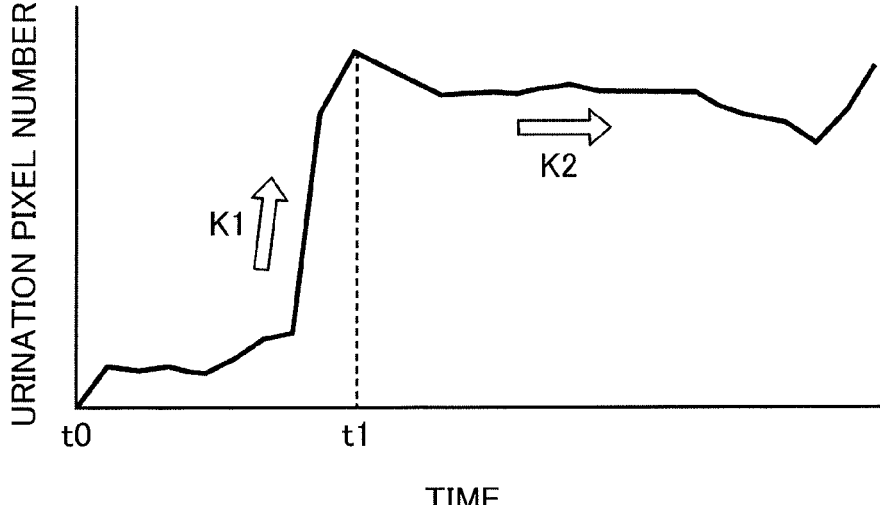
FIG. 8 is a graph showing a change in the urination pixel number over time about a person having a large flow momentum value and a normal urine specific gravity.

FIG. 8 is a graph showing a change in the urination pixel number over time about a person having a large flow momentum value and a normal urine specific gravity. It is seen from a urination period for a person having a large flow momentum value as shown in FIG. 8 that the urination pixel number rapidly increases with an average slope K1 at a later stage of the urination period. The person having the normal urine specific gravity has a small urine specific gravity, and thus, a quantity of urine sinking into the bottom of the pool part 104 is also small. Thus, the average slope K2 of the urination pixel number after the time t1 in FIG. 8 is gentler than the average slope K2 shown in FIG. 7.

From these perspectives, the change in the urination pixel number over time has a waveform that varies depending on the flow momentum value, the urine quantity, and the urine specific gravity. Conclusively, the analysis of the change in the urination pixel number leads to achievement in calculation of the flow momentum value, the urine quantity, and the urine specific gravity.

This disclosure can adopt modifications described below.

(1) In step S31 in FIG. 6, the second calculation part 113 calculates a flow momentum value by using the equation (1), but this is just an example, and the second calculation part may calculate a maximum value $\Delta P_{max}$ as the flow momentum value.

(2) In step S32 in FIG. 6, the second calculation part 113 calculates a urine quantity by using the equation (2), but this is just an example, and the second calculation part may calculate an absolute value of the first integral value TP1, or the first integral value TP1 as the urine quantity.

(3) Although each of sitting and leaving is detected on the basis of a distance value from the sitting sensor 21 in the embodiment, this is just an example. Each of the sitting and the leaving may be detected on the basis of an illuminance value from the illuminance sensor 22. In this case, when the illuminance value is equal to or lower than a sitting detection threshold related to illuminance, the sitting of the user may be detected. When the illuminance value continuously exceeds the sitting detection threshold related to illuminance for a predetermined period or longer, leaving of the user may be detected.

(4) The first integral value TP1 is an integral value of derivative values ΔP, but may be an integral value of the urination pixel number in a period from a urination start to a urination finish.

(5) The second integral value TP2 is an integral value of derivative values ΔP, but may be expressed by "the first integral value TP1 at a urination finish"—"the integral value of the urination pixel number (t) in a period from a urination finish to leaving".

The present disclosure enables grasping of characteristics about urination by a user, and thus is useful for management of health of the user based on the characteristics about the urination.

The invention claimed is:

1. A urination analysis method for a urination analysis device that analyzes urination, the urination analysis method comprising:

by a processor included in the urination analysis device,
    acquiring image data captured by a camera which is located at a toilet to photograph a bowl of the toilet;
    calculating a urination pixel number being a number of pixels of an image showing urination from the image data when the urination by a user is detected by image recognition of the image data;
    calculating, based on a change in the urination pixel number, at least one of a flow momentum value indicating flow momentum of the urination, a urine quantity indicating a quantity of urine, and a urine specific gravity indicating a specific gravity of the urine; and
    outputting the at least one of the flow momentum value, the urine quantity, and the urine specific gravity,
wherein the urine specific gravity is calculated based on a first integral value of decrease amounts per unit time with respect to the urination pixel number.

2. The urination analysis method according to claim 1, wherein the flow momentum value is calculated based on a maximum value in increase amounts per unit time with respect to the urination pixel number.

3. The urination analysis method according to claim 2, wherein the flow momentum value is calculated based on the maximum value in the increase amounts and the urine specific gravity.

4. The urination analysis method according to claim 2, wherein,
    in the calculating of the flow momentum value, a maximum value in derivative values of the urination pixel number in a period from a urination start to a urination finish is calculated as the maximum value in the increase amounts.

5. The urination analysis method according to claim 1, wherein the urine quantity is calculated based on a second integral value of increase amounts per unit time with respect to the urination pixel number.

6. The urination analysis method according to claim 5, wherein the urine quantity is calculated based on the second integral value and the urine specific gravity.

7. The urination analysis method according to claim 5, wherein,
    in the calculating of the urine quantity, the second integral value is calculated based on derivative values of the urination pixel number in a period from a urination start to a urination finish.

8. The urination analysis method according to claim 1, wherein,
    in the calculating of the urine specific gravity, the first integral value is calculated based on derivative values of the urination pixel number in a period from a urination finish to leaving of the user from the toilet.

9. The urination analysis method according to claim 1, wherein,
    in the detecting of the urination, the urination is detected when the image data includes pixel data in which a green/red (G/R) value, a blue/red (B/R) value, a red (R) value, a green (G) value, and a blue (B) value satisfy a predetermined urine condition.

10. A urination analysis device that analyzes urination, comprising:
    a processor; and
    a memory including a program that, when executed by the processor, causes the processor to:
        acquire image data captured by a camera which is located at a toilet to photograph a bowl of the toilet;
        calculate a urination pixel number being a number of pixels of an image showing urination from the image data when the urination by a user is detected by image recognition of the image data;
        calculate, based on a change in the urination pixel number, at least one of a flow momentum value indicating flow momentum of the urination, a urine quantity indicating a quantity of urine, and a urine specific gravity indicating a specific gravity of the urine; and
        output at least one of the flow momentum value, the urine quantity, and the urine specific gravity,
    wherein the urine specific gravity is calculated based on an integral value of decrease amounts per unit time with respect to the urination pixel number.

11. A non-transitory computer readable recording medium storing a urination analysis program causing a computer to serve as a urination analysis device that analyzes urination, the urination analysis program comprising:
    further causing the computer to execute:
        acquiring image data captured by a camera which is located at a toilet to photograph a bowl of the toilet;
        calculating a urination pixel number being a number of pixels of an image showing urination from the image data when the urination by a user is detected by image recognition of the image data;
        calculating, based on a change in the urination pixel number, at least one of a flow momentum value indicating flow momentum of the urination, a urine quantity indicating a quantity of urine, and a urine specific gravity indicating a specific gravity of the urine; and
        outputting the at least one of the flow momentum value, the urine quantity, and the urine specific gravity, wherein the urine specific gravity is calculated based on an integral value of decrease amounts per unit time with respect to the urination pixel number.

* * * * *